United States Patent [19]

Ruechardt et al.

[11] Patent Number: 4,691,020
[45] Date of Patent: Sep. 1, 1987

[54] PREPARATION OF OPTICALLY ACTIVE CARBOXYLIC ACIDS

[75] Inventors: Christoph Ruechardt, Stegen b. Freiburg; Joachim Jaehme; Ulrich Salz, both of Freiburg, all of Fed. Rep. of Germany

[73] Assignee: BASF Aktiengesellschaft, Ludwigshafen, Fed. Rep. of Germany

[21] Appl. No.: 632,700

[22] Filed: Jul. 23, 1984

Related U.S. Application Data

[63] Continuation of Ser. No. 363,503, Mar. 30, 1982, abandoned.

[30] Foreign Application Priority Data

Apr. 25, 1981 [DE] Fed. Rep. of Germany ....... 3116474

[51] Int. Cl.[4] .................. C07D 213/55; C07D 401/06; C07C 59/84; C07C 59/86
[52] U.S. Cl. .................................. 546/341; 546/261; 546/301; 546/302; 562/466; 562/471; 562/472; 562/493
[58] Field of Search .............. 546/341, 261, 301, 302; 562/471, 472, 466, 493

[56] References Cited

PUBLICATIONS

March, Advanced Organic Chemistry, Second Edition, pp. 106–111, 349–351, 936, 937 & 944, McGraw-Hill Pub.
Pracejus, Liebigs Annalen der Chemie, vol. 634, pp. 9–29, (1960).
Von Ernst Anders et al., Angewandte Chemie, vol. 85, pp. 16–20, (1973).
PAS Smith, The Chem. of Open–Chain Organic Nitrogen Compounds, vol. I, pp. 152, 153 and 211–213, Benjamin Pub. 1965.
P.A.S. Smith, The Chem. of Open–Chain Organic Nitrogen Compounds, vol. 2, p. 405, Benjamin Pub. 1965.
Liebigs Annalen der Chemie, vol. 634 (1960), pp. 9–29.
Angewandte Chemie, vol. 85 (1973), pp. 16–20.

Primary Examiner—Alan L. Rotman
Attorney, Agent, or Firm—Keil & Weinkauf

[57] ABSTRACT

Optically active carboxylic acids

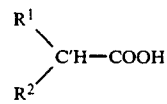

where $R^1$ is an organic radical which is linked to the asymmetric $C'$ atom via a carbon atom and $R^2$ is one of the radicals $R^1$ (but not the same radical), halogen or an organic radical which is bonded to the asymmetric $C'$ atom via an oxygen atom, are prepared by reacting a ketene II

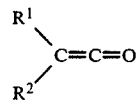

with an alcohol in a homogeneous liquid phase in the presence of a tertiary amine III and then converting the resulting ester into the acid, using an optically active alcohol IV.

3 Claims, No Drawings

PREPARATION OF OPTICALLY ACTIVE CARBOXYLIC ACIDS

This application is a continuation of application Ser. No. 363,503, filed on Mar. 30, 1982, abandoned.

The present invention relates to an improved process for the preparation of optically active carboxylic acids of the general formula I

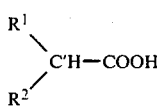

where $R^1$ is an organic radical which is linked to the asymmetric C' atom via a carbon atom and $R^2$ is one of the radicals $R^1$ (but not the same radical), halogen or an organic radical which is bonded to the asymmetric C' atom via an oxygen atom.

A paper by Pracejus (Liebigs Annalen der Chemie, 634 (1960), 9 et seq.) discloses the reaction of methylphenylketene with an achiral alcohol in the presence of an optically active tertiary amine, such as brucine, to give the corresponding carboxylic acid ester:

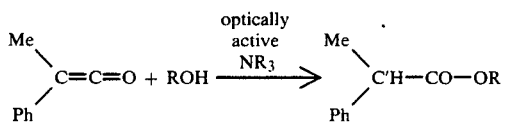

Me=methyl
Ph=phenyl one of the two optically isomeric esters being preferentially formed. The optical yield (=% of the predominantly isomer minus % of the other isomer) in this reaction is, however, only 2-10%, corresponding to an isomer ratio of from 51:49 to 55:45, unless the reaction is carried out at extremely low temperatures. This process is therefore unsuitable for industrial synthesis of optically active carboxylic acid esters or their secondary products, such as the free acids.

A paper by Anders et al. (Angew. Chem. 85 (1973), 16 et seq.) moreover discloses that phenyltrifluoromethylketene can be converted into a corresponding ester using an optically active secondary alcohol in the absence of an amine. Analysis of the free carboxylic acid of type I ($R^1$=phenyl, $R^2$=trifluoromethyl) obtained therefrom by hydrolysis showed that in each case one of the isomers had been formed in excess, corresponding to an optical yield of from 22 to 36%. However, even these results are not adequately satisfactory.

It is an object of the present invention to prepare the carboxylic acids I in a more economical and a technologically simpler manner and in a higher optical purity than hitherto.

We have found that this object is achieved and that the carboxylic acids I defined above are obtained in an unexpectedly high optical yield by reacting a ketene II

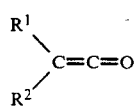

with an alcohol in a homogeneous liquid phase in the presence of a tertiary amine III and then converting the resulting ester into the acid, by a process wherein an optically active alcohol IV is used.

In an advantageous modification of this process, it is also possible to use an optically active tert.-aminoalcohol, ie. a compound combining the functions of III and IV, instead of the amine III and the alcohol IV.

Our observations have so far shown that the success of the process according to the invention is substantially independent of the chemical nature of $R^1$ and $R^2$ in the starting compounds II, so that these radicals can in principle be chosen as desired. Essentially, only steric effects have an influence on the optical yield, which in any case does not usually fall below 30%. However, so that the carbon atom carrying these radicals can become chiral, neither of these radicals may denote hydrogen and they may not be identical.

Suitable radicals $R^1$ include aliphatic radicals of 1 to 20 carbon atoms, eg. alkyl, $C_2$-$C_{20}$-alkenyl, and $C_2$-$C_{20}$-alkynyl, preferably $C_1$-$C_4$-alkyl, cycloaliphatic radicals having 5 or 6 ring members, such as, preferably, cyclopentyl, cyclopentenyl, cyclohexyl and cyclohexenyl, araliphatic radicals, such as, preferably, benzyl, and isocyclic and heterocyclic aromatic radicals, such as, preferably, phenyl, naphthyl and pyridyl. These radicals can in turn carry inert substituents, such as $C_1$-$C_{10}$-alkyl, $C_2$-$C_{10}$-alkenyl, halogen, cyano, nitro, formyl, $C_1$-$C_4$-alkoxy, $C_1$-$C_4$-carbalkoxy, $C_1$-$C_4$-acyl, $C_1$-$C_4$-acyloxy or amino.

Suitable radicals $R^2$ include the radicals $R^1$, with the proviso that $R^2$ may not be the same as $R^1$, and also halogen, eg. fluorine, chlorine, bromine and iodine, and organic radicals which are bonded to the prochiral carbon atom via an oxygen atom. Starting compounds II of the latter type thus have the general formula IIa

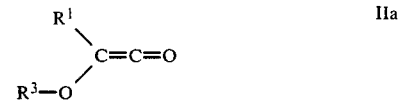

where $R^3$ can be, for example, one of the radicals $R^1$.

Those ketenes II which are not already known can be obtained in a conventional manner, and, in particular, preferably by reacting the corresponding acid chloride II' with a tertiary amine

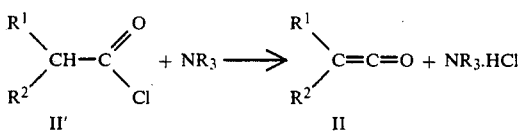

As it is not necessary to isolate the ketene II before the reaction according to the invention, it is particularly advantageous in industrial operation to use the reaction mixture obtained in situ in the preparation of the ketene II, for example from the carboxylic acid chloride II', especially since the same tertiary amine III can be used for both reactions.

The tertiary amine III required for the reaction according to the invention can be any desired tertiary nitrogen base, eg. a trialkylamine having $C_1$-$C_{20}$-alkyl radicals, such as trimethylamine, triethylamine, tributylamine or dimethylstearylamine, a cycloaliphatic amine such as N-methylpyrrolidone, N-methylpiperidine or N-methylmorpholine, an aromatic amine such as dimethylaniline, or a heterocyclic nitrogen base such as pyridine or quinoline. Polycyclic bridgehead amines such as 1,4-diazabicyclo-[2.2.2]-octane ("DABCO") are particularly suitable.

It is an essential feature of the invention that the tertiary amine III does not need to be optically active as in the above process disclosed by Pracejus, but the optical yield can in some cases be increased further if an optically active tertiary amine, eg. an optically active 1,2-dimethylpiperidine or N,N-dimethyl-1-phenylethylamine, is used. Which of the two enantiomers influences the reaction in the desired manner (in some circumstances, the other enantiomer can impede the reaction) can be determined by a simple preliminary experiment.

Since the reaction according to the invention probably proceeds via an intermediate of the type

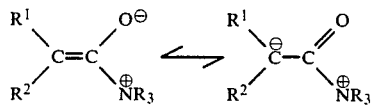

which offers to the proton of the optically active alcohol IV a preferred direction of entry into the molecule, it is advisable to use a sufficient amount of the tertiary amine III so that this effect is not blanketed by a less specific addition reaction of the alcohol, as is to be observed in the absence of an amine. From 0.5 to 1 mole of the amine III per mole of II is therefore generally used, but even smaller amounts (down to 0.1 mole) are frequently sufficient. In some cases, a stoichiometric excess of the amine of not more than about 10 moles may also be advantageous.

If the ketene II is not isolated for the process according to the invention but is formed in situ, for example from the carboxylic acid chloride II', the total amount of amine required for both reaction steps is preferably employed, ie. from 1.1 to 10 moles, preferably from 1.5 to 2 moles, per mole of II'. Since a strongly basic amine is as a rule required for ketene formation, where an amine in which the N atom is substantially free from steric hindrance, as in the case of (relatively weakly basic) pyridine or DABCO, is preferred for the step according to the invention, it is frequently also advisable to use two different amines.

As long as the alcohol IV is only optically active, experience gained so far has shown that the type of alcohol has in principle no influence on the success of the process according to the invention. Although the chirality center can essentially be in any desired position in the molecule, the best results are achieved with alcohols in which the hydroxyl group is on a chiral C atom. Moreover, it is immaterial whether the alcohol has one or more chirality centers.

Examples of suitable asymmetric alcohols are the optical isomers of isocyclic and heterocyclic 1-aryl-$C_1$-$C_4$-alkan-1-ols, in which the aryl group can be substituted by, inter alia, $C_1$-$C_4$-alkyl, $C_1$-$C_4$-alkoxy, halogen, nitro, cyano, dialkylamino or alkyleneamino, such as N-pyrrolidino and N-piperidino. Preferred aryl groups are naphthyl, pyridyl and, in particular, phenyl. The simplest and therefore frequently particularly preferred alcohol is 1-phenylethan-1-ol. Optically active terpene alcohols, such as menthol, and optically active aminoalcohols IV', such as N-methylephedrine(1-phenyl-2-dimethylamino-propan-1-ol) and 2-amino-butan-1-ol, are also suitable. If aminoalcohols are used, the use of a separate amine III may of course be superfluous.

Not less than the stoichiometric amount of the alcohol IV, but preferably an excess (of not more than about 10 moles), based on the ketene II, is used.

The reaction is otherwise carried out as a conventional adduct formulation of an alcohol with a ketene. The reaction temperature is advantageously from $-80°$ to $100°$ C., and the stereospecific selectivity usually decreases as the temperature increases. However, since satisfactory optical yields of more than 60% are as a rule achieved even at room temperature, it is not usually worth reducing the temperature in order to achieve only a relatively slight increase in optical yield.

Suitable solvents are aprotic liquids such as benzene, toluene, $C_4$-$C_8$-alkanes, cyclohexane, ethers, such as dimethyl ether, diethyl ether and cyclic ethers, such as dioxane and tetrahydrofuran, and haloalkanes, e.g. dioxane and chloride. A 1–20% strength solution is preferably used. When the reaction has ended, the mixture is worked up in a conventional manner, by distilling the solvent, the excess amine III and the excess alcohol from the resulting ester I'

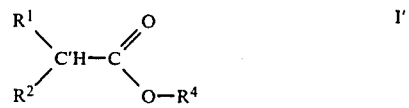

where $R^4$ is a radical of the alcohol $R^4OH$ (IV), fractionation of these components not being necessary if they are to be used for a further reaction batch. If the carboxylic acid chloride II' has been used as the starting material, the ammonium chloride $R_3N.HCl$, which is usually obtained in the form of crystals, is separated off before further working up.

The ester I' is then split in a conventional manner, for example with dilute hydrochloric acid or with dilute sodium hydroxide solution at $30°$–$100°$ C., into the acid I or the Na salt of the acid on the one hand and the alcohol IV, after which the alcohol can be recycled to the reaction. The acid is isolated in a conventional manner and, if desired, purified.

Since no substantial amounts of either the amine III or the alcohol IV are consumed, the process according to the invention ultimately consists of converting a (prochiral) ketene II or its intermediate, ie. a racemic carboxylic acid chloride II', into an optically active carboxylic acid I with a high optical yield. It is advantageous that the process is evidently particularly suitable for continuous operation.

Optical yields of not less than 30%, but in most cases from 70 to 80%, are as a rule achieved. Whether the R-isomer or the S-isomer is formed in excess cannot be reliably predicted, but the R/S ratio is reversed if the antipodal alcohol is used.

The products I are either important active compounds per se or intermediates for the preparation of physiologically active substances. As readily accessible optically active acids, they are in turn also suitable for resolving racemic alcohols via diastereomeric pairs of compounds.

EXAMPLE 1

Preparation of R-hydratropic acid

(2-Phenylpropionic acid)

A solution of 1.0 g (10 mmoles) of triethylamine and 25 ml of toluene was added to a solution of 1.6 g (10 mmoles) of R,S-hydratropic acid chloride and 50 ml of toluene at 0° C., after which this solution was stirred at 0° C. for 30 minutes and at 25° C. for 3 hours. The solution became yellow and a white precipitate was formed.

A solution of 0.8 g (10 mmoles) of pyridine and 1.6 g (10 mmoles) of 1-menthol (2-isopropyl-5-methylcyclohexanol) was then added rapidly to this mixture at 0° C., and the mixture was kept at 0° C. for a further 3 hours. It was then stirred with 50 ml of concentrated hydrochloric acid at 50° C. for 12 hours, after which the aqueous phase was separated off and the organic phase was worked up to hydratropic acid in a conventional manner.

The acid was purified by bulb tube distillation (yield: 78%) and had an optical rotation $[\alpha]_D^{22}$ (acetone) of $(-36.0)°$. This corresponds to an optical yield of 38% of R-hydratropic acid, or an enantiomer ratio of 69:31.

EXAMPLE 2

Preparation of S-2-phenoxypropionic acid

This acid was prepared in an optical yield of 28%, corresponding to an enantiomer ratio of 64:36, from R,S-2-phenoxypropionyl chloride, triethylamine, pyridine and S-1-phenylethanol by a method similar to that in Example 1.

EXAMPLE 3

Preparation of S-hydratropic acid

A solution of 0.6 mmole of triethylamine, 0.6 mmole of pyridine, 0.07 g (0.6 mmole) of S-1-phenylethanol and 4 ml of toluene was added to a solution of 0.1 g (0.6 mmole) of R,S-hydratropic acid chloride and 2 ml of toluene at 0° C., and the mixture was worked up to give S-hydratropic acid by a method similar to that in Example 1.

The optical yield of S-hydratropic acid was 60%. When the same molar amount of 1,4-diazabicyclo-[2.2.2]-octane (DABCO) was used as the tertiary amine instead of the triethylamine and the pyridine, the optical yield was 72%.

EXAMPLE 4

Preparation of R-hydratropic acid

R-Hydratropic acid was obtained, by a method similar to that in Example 3, but with R-1-phenylethanol, in an optical yield of 72% when triethylamine and pyridine were used and in an optical yield of 74% when DABCO was used.

EXAMPLE 5

Preparation of (+)-2-(6-methoxynaphth-2-yl)-propionic acid 0.12 g (1.2 mmoles) of triethylamine was added to a solution of 0.3 g (1.2 mmoles) of racemic 2-(6-methoxynaphth-2-yl)-propionyl chloride and 20 ml of toluene at 0° C., the mixture was stirred at 25° C. for 3 hours and then combined with a solution of 0.1 g (1.2 mmoles) of pyridine, 0.15 g (1.2 mmoles) of S-1-phenylethanol and 20 ml of toluene at 0° C., and stirring was continued for 2 hours. Conventional working up gave the above acid in an optical yield of 57%.

EXAMPLE 6

Preparation of S-2-chloro-phenylacetic acid

This compound was prepared in an optical yield of 47% from 2-chloro-phenylacetyl chloride and 1-phenylethanol, using diethyl ether as the solvent, by a method similar to that in Example 5.

EXAMPLE 7

Preparation of S-hydratropic acid 1.32 g (10 mmoles) of phenylmethylketene and 1.78 g (10 mmoles) of (+)-N-methylpseudophedrin (1-phenyl-2-dimethylamino-propan-1-ol) were reacted with one another in about 10% strength toluene solution at 70° C., after which the reaction mixture was further processed by a method similar to that in Example 1. S-Hydratropic acid was obtained in an optical yield of 32%.

EXAMPLE 8

Preparation of S-hydratropic acid 1.32 g (10 mmoles) of phenylmethylketene were reacted with 1.22 g (10 mmoles) of S-1-phenylethanol at 0° C. in about 10% strength toluene solution in the presence of 1.5 g (10 mmoles) of S-N-dimethyl-1-phenylethylamine (optical purity: 96%), and the mixture was worked up to give the hydratropic acid by a method similar to that in Example 1. The optical yield of S-hydratropic acid was 80%, corresponding to an enantiomer ratio of 90:10.

When the antipodal amine was used under otherwise identical conditions, the optical yield of S-hydratropic acid was 58%, corresponding to an enantiomer ratio of 79:21.

We claim:

1. A process for the preparation of an optically active carboxylic acid of the formula I

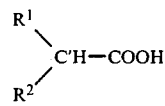

wherein $R^1$ is an unsubstituted or substituted alkyl radicals of 1 to 20 carbon atoms, unsubstituted or substituted alkenyl or alkynyl radicals having 2–20 carbon atoms, an unsubstituted or substituted cycloalkyl or cycloalkenyl radicals having 5 or 6 ring members, an unsubstituted or substituted benzyl, phenyl, naphthyl or pyridyl radical wherein substituted represents a member selected from the group consisting of $C_1$–$C_{10}$-alkyl, $C_2$–$C_{10}$-alkenyl, halogen, formyl, $C_1$–$C_4$-alkoxy, $C_1$–$C_4$-Carbalkoxy, $C_1$–$C_4$-acyl, $C_1$–$C_4$-acyloxy or amino which is linked to the asymmetric C' atom via a carbon atom and $R^2$ is one of the radicals $R^1$ (but not the same radical) or halogen which is bonded to the asymmetric C' atom via an oxygen atom, which process comprises reacting a ketene II

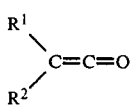

with an optically active alcohol in a homogeneous liquid phase in the presence of from 0.1 to 10 moles of a tertiary amine III per mole of ketene II and then converting the resulting ester into the acid I.

2. A process as set forth in claim 1, wherein a solution of a ketene II which has been prepared in situ from a carboxylic acid chloride II′

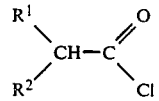

and a tertiary amine is used.

3. A process as set forth in claim 1, wherein $R^1$ is the radical $C_1$–$C_4$-alkyl, cyclopentyl, cyclopentenyl, cyclohexyl, cyclohexenyl, benzyl, phenyl, naphthyl or pyridyl, and such radicals bearing an inert substituent selected from the group consisting of $C_1$–$C_{10}$-$C_2$–$C_{10}$, or, -alkenyl, halogen, formyl, $C_1$–$C_4$-alkoxy, $C_1$–$C_4$-carbalkoxy, $C_1$–$C_4$-acyl, $C_1$–$C_4$-acyloxy or amino.

* * * * *